US012079985B2

(12) United States Patent
Chen et al.

(10) Patent No.: US 12,079,985 B2
(45) Date of Patent: Sep. 3, 2024

(54) DIABETIC RETINOPATHY DETECTION USING MACHINE LEARNING

(71) Applicant: Acer Medical Inc., New Taipei (TW)

(72) Inventors: Ming-ke Chen, New Taipei (TW); Chin-Han Tsai, New Taipei (TW)

(73) Assignee: Acer Medical Inc., New Taipei (TW)

( * ) Notice: Subject to any disclaimer, the term of this patent is extended or adjusted under 35 U.S.C. 154(b) by 454 days.

(21) Appl. No.: 17/354,837

(22) Filed: Jun. 22, 2021

(65) Prior Publication Data

US 2022/0301153 A1 Sep. 22, 2022

(30) Foreign Application Priority Data

Mar. 19, 2021 (TW) ................................ 110109981

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/7267* (2013.01); *G06N 3/04* (2013.01);
(Continued)

(58) Field of Classification Search
CPC ......... G06T 7/0012; G06T 2207/20081; G06T 2207/30041; A61B 5/7267; G06N 3/04; G16H 30/40; G16H 70/60
See application file for complete search history.

(56) References Cited

U.S. PATENT DOCUMENTS

2017/0357879 A1* 12/2017 Odaibo .................. G06N 3/044
2021/0012884 A1* 1/2021 Kim ..................... G06T 7/0012
(Continued)

FOREIGN PATENT DOCUMENTS

CN 111798464 10/2020
CN 112418329 2/2021
(Continued)

OTHER PUBLICATIONS

Deng et al., "Imagenet: A large-scale hierarchical image database," IEEE Conference on Computer Vision and Pattern Recognition, Jun. 2009, 8 pages.
(Continued)

*Primary Examiner* — Casey L Kretzer
(74) *Attorney, Agent, or Firm* — JCIPRNET (57) ABSTRACT

Methods, systems, and apparatus, including computer programs encoded on a computer storage medium, for computer aided diagnosis of a medical image. One of the methods includes processing the medical image through a machine learning (ML) model to provide a first feature representation of the medical image, wherein the ML model includes an input layer and a pooling layer, wherein the first feature representation is an output from the pooling layer, generating, by the ML model, a sequence of second feature representations of the medical image from the first feature representation of the medical image, wherein each second feature representation in the sequence of the second feature representations having a lower dimension than the first feature representation, and generating, by the ML model, an output as a last second feature representation in the sequence of the second feature representations.

18 Claims, 5 Drawing Sheets

(51) Int. Cl.
    *G06N 3/04* (2023.01)
    *G16H 30/40* (2018.01)
    *G16H 70/60* (2018.01)

(52) U.S. Cl.
    CPC .............. *G16H 30/40* (2018.01); *G16H 70/60* (2018.01); *G06T 2207/20081* (2013.01); *G06T 2207/30041* (2013.01)

(56) References Cited

U.S. PATENT DOCUMENTS

| | | | |
|---|---|---|---|
| 2021/0177373 A1* | 6/2021 | Xie | A61B 8/14 |
| 2023/0008386 A1* | 1/2023 | Nahum | G06N 3/08 |
| 2023/0196803 A1* | 6/2023 | Roessler | G06V 20/698 382/181 |

FOREIGN PATENT DOCUMENTS

| | | | |
|---|---|---|---|
| JP | 2004535569 | 11/2004 | |
| JP | 2019152968 | 9/2019 | |
| JP | 2019211913 | 12/2019 | |
| JP | 2020103880 | 7/2020 | |
| TW | I696145 | 6/2020 | |
| TW | I704903 | 9/2020 | |
| WO | 2019220622 | 11/2019 | |
| WO | 2019245597 | 12/2019 | |
| WO | WO-2020020809 A1 * | 1/2020 | A61B 8/085 |

OTHER PUBLICATIONS

He et al., "Deep residual learning for image recognition," Proceedings of the IEEE Conference on Computer Vision and Pattern Recognition, Jun. 2016, 9 pages.
Lin et al., "Feature pyramid networks for object detection" In 2017 IEEE Conference on Computer Vision and Pattern Recognition, Jul. 2017, 9 pages.
Simonyan et al., "Very deep convolutional networks for large-scale image recognition," arXiv preprint arXiv:1409.1556, Sep. 2014, 14 pages.
Szegedy et al., "Inception-v4, inception-resnet and the impact of residual connections on learning," Proceedings of the AAAI Conference on Artificial Intelligence, Feb. 2017, 31(1):7 pages.
Kimura et al., "Machine Learning based Prediction of DPC from Discharge Summaries", Japan Association Medical Informatics, with English abstract, Nov. 21, 2019, pp. 684-689.
Wei Zhang et al., "DeepUWF-plus: automatic fundus identification and diagnosis system based on ultrawide-field fundus imaging", Applied Intelligence, Mar. 12, 2021, pp. 7533-7551.
Linyi Li et al., "Case Study: Explaining Diabetic Retinopathy Detection Deep CNNs via Integrated Gradients", Artificial Intelligence, Sep. 27, 2017, pp. 1-10.
Muhammad Naufal Rachmatullah et al., "Low Resolution Image Fish Classification Using Convolutional Neural Network", 2018 5th International Conference on Advanced Informatics: Concept Theory and Applications (ICAICTA), Aug. 14, 2018, pp. 78-83.
Yi-Ting Hsieh et al., "Application of deep learning image assessment software VeriSee™ for diabetic retinopathy screening", Journal of the Formosan Medical Association, Apr. 16, 2020, pp. 165-171.
"Search Report of Europe Counterpart Application", issued on Feb. 22, 2022, p. 1-p. 10.

* cited by examiner

FIG. 5

DIABETIC RETINOPATHY DETECTION USING MACHINE LEARNING

CROSS-REFERENCE TO RELATED APPLICATION

This application claims priority to Taiwan Patent Application No. 110109981, entitled "Detecting Method and Detecting Apparatus Related to Image," filed Mar. 19, 2021, which is incorporated herein by reference in its entirety.

BACKGROUND

Diabetic retinopathy (DR) is one of the major microvascular complications in diabetes mellitus. Many patients who have diabetes can develop DR, and some of the patients may suffer visual loss if the detection of DR is delayed. Initial screening of DR can be accomplished with a fundus examination (i.e., retinal photography). Fundus examination is a routine examination in ophthalmology that generates a photography of the rear of an eye (i.e., the fundus). Ophthalmologists can use specialized fundus cameras to capture the fundus image.

DR is able to be detected in the fundus image generated in the fundus examination. However, a large number of diabetic patients do not receive DR screenings regularly. This results in delayed diagnosis of DR in many patients, and these patients cannot receive timely referral or treatment.

One of the reasons for the poor DR screening rate is the lack of a sufficient number of well-trained ophthalmologists. Many general practitioners or internal medicine physicians (e.g., a home doctor, a metabolist) are not specialized in diagnosing DR in the fundus images. Without an automatic solution, the ophthalmologists have to visually inspect the fundus images, including reviewing the subtle vascular structures and their changes. After continuously reviewing a large number of fundus images, an ophthalmologist can become fatigued and can miss small lesions in the fundus image. When the image quality of the fundus image is poor, or when the ophthalmologist reads the fundus image in an environment with bright background light, the ophthalmologist may make mistakes in detecting DR in the fundus image.

SUMMARY

Implementations of the present disclosure are generally directed to computer-implemented systems for computer aided diagnosis of a medical image. More particularly, implementations of the present disclosure are directed to computer aided diagnosis of diabetic retinopathy (DR) in a fundus image using machine learning.

In general, one innovative aspect of the subject matter described in this specification can be embodied in methods that include the actions of processing the medical image through a machine learning (ML) model to provide a first feature representation of the medical image, wherein the ML model includes an input layer and a pooling layer, wherein the first feature representation is an output from the pooling layer; generating, by the ML model, a sequence of second feature representations of the medical image from the first feature representation of the medical image, wherein each second feature representation in the sequence of the second feature representations having a lower dimension than the first feature representation; and generating, by the ML model, an output as a last second feature representation in the sequence of the second feature representations. Other embodiments of this aspect include corresponding computer systems, apparatus, and computer programs recorded on one or more computer storage devices, each configured to perform the actions of the methods. For a system of one or more computers to be configured to perform particular operations or actions means that the system has installed on its software, firmware, hardware, or a combination of them that in operation cause the system to perform the operations or actions. For one or more computer programs to be configured to perform particular operations or actions means that the one or more programs include instructions that, when executed by a data processing apparatus, cause the apparatus to perform the operations or actions.

The foregoing and other embodiments can each optionally include one or more of the following features, alone or in combination. In particular, one embodiment includes all the following features in combination. Generating, by the ML model, the sequence of the second feature representations of the medical image from the first feature representation of the medical image includes: processing the first feature representation through a sequence of layers to generate the sequence of the second feature representations, wherein an output dimension of a next layer in the sequence of layers is less than an output dimension of a current layer. The sequence of layers includes one or more of fully-connected layers or convolutional layers. The output dimension of the sequence of layers is an arithmetic sequence, or a geometric sequence. All neurons in the sequence of layers are being used during training and inference of the ML model. The actions further include providing a plurality of ML models, each ML model including an input layer and a pooling layer; generating, by the plurality of ML models, a plurality of respective outputs; and generating a final output by calculating an ensemble of the plurality of the respective outputs. The final output is one of a weighted average of the plurality of the respective outputs and a root mean-squared value of the plurality of the respective outputs. Each ML model includes a modified Inception-V4 model, and the pooling layer includes an average pooling layer. The medical image is a fundus image, and the output is a classification result indicating whether diabetic retinopathy is detected in the fundus image.

Particular embodiments of the subject matter described in this specification can be implemented to realize one or more of the following advantages.

The computer aided diagnosis system described in the present disclosure can make reliable, accurate and fast computer aided diagnosis. The system can accurately detect DR in the fundus images using a machine learning model (e.g., a deep neural network). Typically, a deep neural network model can include a dropout layer to overcome overfitting. However, dropout technique may significantly increase training time and reduce training speed. Rather than using a dropout layer that slows down training, the machine learning model includes a feature reduction module that can prevent overfitting to a particular set of training data as well as reducing the required training time. The feature reduction module includes a sequence of feature reduction layers that generate a sequence of feature representations with sequentially reducing sizes and thus reduce the effect of unimportant features.

The machine learning model includes a feature extraction module that is sensitive to small lesions and small vascular structures in the fundus images. Prediction outputs from multiple machine learning models can be aggregated to generate an ensemble output for improved detection accuracy. Furthermore, the automated system can provide reliable and accurate diagnosis results even when the image quality is not optimal.

The computer aided diagnosis system is fully automatic, and can provide good sensitivity and specificity in detecting DR in the fundus images. The automated system can provide assistance to general practitioners and internal medicine physicians in detecting DR. The automated system can also reduce the workload for ophthalmologists. Furthermore, the automated system can provide assistance to the ophthalmologists when they are tired, or when the image viewing environment is not ideal (e.g., when the environment includes a bright background light).

The details of one or more implementations of the present disclosure are set forth in the accompanying drawings and the description below. Other features and advantages of the present disclosure will be apparent from the description and drawings, and from the claims.

BRIEF DESCRIPTION OF DRAWINGS

Like reference symbols in the various drawings indicate like elements.

DETAILED DESCRIPTION

Implementations of the present disclosure are directed to computer aided diagnosis of diabetic retinopathy (DR) in a fundus image using machine learning.

In general, ophthalmologists can grade the severity of DR in multiple levels, for example, no DR, mild non-proliferative diabetic retinopathy (NPDR), moderate NPDR, severe NPDR, and proliferative diabetic retinopathy (PDR). Referable DR can be defined as moderate NPDR or worse.

Figure 1:
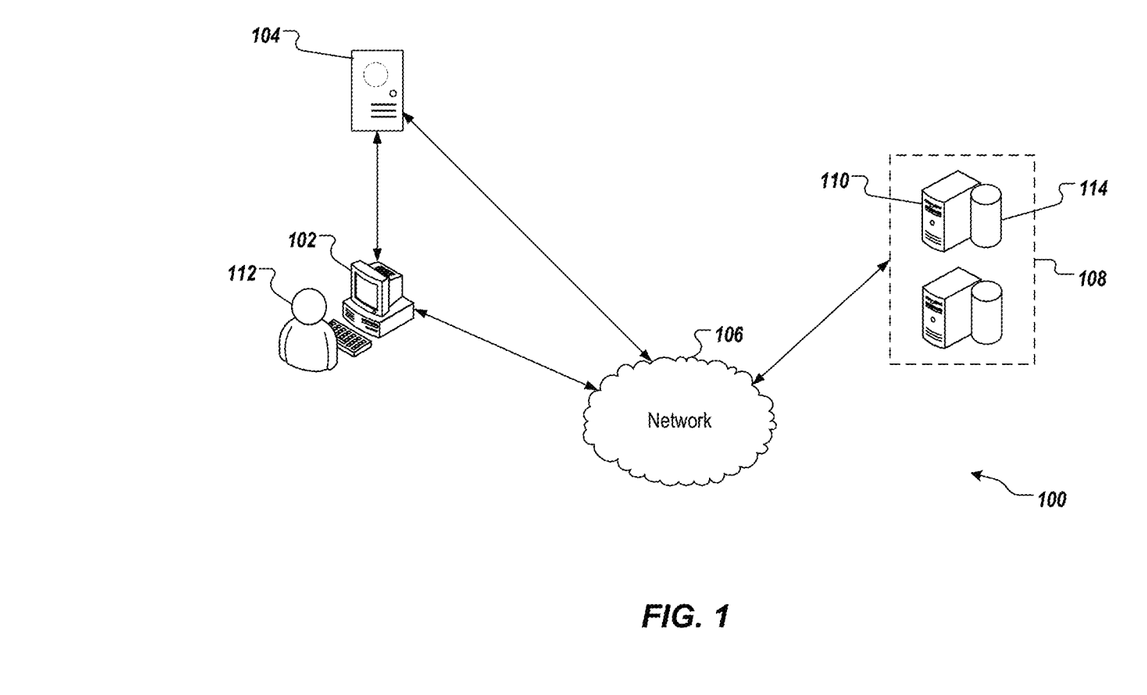
FIG. 1 depicts an example system that can execute implementations of the present disclosure.

FIG. 1 depicts an example system 100 that can execute implementations of the present disclosure. The example system 100 includes a fundus camera 104, a client device 102, a server system 108, and a network 106. In some examples, the network 106 includes a local area network (LAN), wide area network (WAN), the Internet, or a combination thereof, and connects web sites, devices (e.g., the fundus camera 104, the client device 102), and remote server systems (e.g., the server system 108). In some examples, the network 106 can be accessed over a wired and/or a wireless communications link.

The fundus camera 104 is a specialized medical device that can capture a photograph of the fundus. The fundus camera 104 can generate a fundus image which shows the structures of the eye, including central and peripheral retina, optic disc, macula, blood vessels, and so on. The fundus camera can capture a photograph of the fundus over a predetermined field of view (e.g., 45 degrees to 55 degrees of the retinal area). Some fundus cameras can include a wide-angle lens that can capture a wider field of view (e.g., 120 degrees, or up to 140 degrees field of view). Ophthalmologists can use the fundus camera 104 in an eye exam to detect and diagnose potential DR conditions in a patient.

In some implementations, the fundus images generated by the fundus camera 104 can be stored in a local database in the hospital for future review. For example, the fundus image can be stored in the client device 102 located in the hospital. In some implementations, the fundus images generated at the hospital can be uploaded to a remote database that is located outside of the hospital. For example, a fundus image can be uploaded to the remote database 114 at a remote server system 108 through the network 106.

The client device 102 can store and display a fundus image captured by the fundus camera 104. A doctor 112 (e.g., an ophthalmologist, a home doctor, a metabolist) can perform visual inspection of the fundus image displayed on the client device 102 and can diagnose various medical conditions that can be found from the fundus image, such as the DR condition. For example, a home doctor who is not specialized in ophthalmology can be assisted by the computer aided diagnosis system described by the systems and techniques in this disclosure to perform diagnosis of various medical conditions that can be found from the fundus image. The client device 102 can include any appropriate type of computing device, such as a desktop computer, a laptop computer, a handheld computer, a tablet computer, a personal digital assistant (PDA), a cellular telephone, a smart phone, a monitor, or an appropriate combination of any two or more of these devices or other data processing devices.

In some implementations, the client device 102 can implement a computer aided diagnosis system that detects DR in a fundus image using machine learning. The computer aided diagnosis system can include a trained machine learning algorithm to generate a prediction result of one or more medical conditions based on the fundus image, such as a DR condition. In some implementations, the prediction result can include a score that indicates, for example, the likelihood that the fundus image has referable DR. In some implementations, the machine learning algorithm can generate a grading level indicating the severity of DR (e.g., no DR, NPDR, moderate NPDR, severe NPDR, and PDR). The prediction result can be included in a medical report. The client device 102 can display the prediction result and the fundus image on a display device (e.g., a monitor) to the doctor 112. The doctor 112 can make further diagnostic determination based on the fundus image and the prediction result.

For example, when a general practitioner 112 is not sure about his/her own diagnosis decision of a fundus image, the general practitioner can review the DR likelihood score generated by the computer aided diagnosis system. The generate practitioner can make better diagnostic decisions when considering the DR likelihood score generated by the computer aided diagnosis system.

As another example, a home doctor who is not specialized in ophthalmology can perform diagnosis of a fundus image using the computer aided diagnosis system. If the predicted medical condition of the fundus image is referable, e.g., severe NDPR, or PDR, the home doctor can timely refer the patient to an ophthalmologist.

As another example, an ophthalmologist 112 can be overloaded with image review work after eye screenings of hundreds of patients are conducted. The client device 102 can automatically generate prediction results for the corresponding hundreds of fundus images. The ophthalmologist can determine to first review the fundus images that have high likelihood of DR condition. This helps prioritize the workload of the ophthalmologist.

As another example, when the ophthalmologist 112 is fatigued or when the image viewing environment is not ideal (e.g., when the environment includes a bright background light) the ophthalmologist 112 can use the prediction result generated by the computer aided diagnosis system as a second opinion, reducing the mistakes (e.g., missing small lesions) in the diagnosis of the fundus images.

In some implementations, the example system 100 can include a server system 108. The server system 108 includes at least one server 110, and at least one database 114. In some implementations, the server system 108 can receive a fundus image sent from the fundus camera 104 over the network 106. In some implementations, the server system 108 can receive a fundus image sent from the client device 102 over the network 106. The server system 108 can implement the computer aided diagnosis system that detects DR in a fundus image based on a machine learning model. The server system can send a prediction result back to the client device 102 or the fundus camera 104 over the network 106.

In some implementations, the machine learning model can include a deep neural network that employs multiple layers of operations to predict one or more outputs from one or more inputs. The server system 108 can use hardware acceleration or other special-purpose computing devices to implement the operations of one or more layers of the deep neural network. For example, some operations of some layers (e.g., a convolutional layer) may be performed by highly parallelized hardware (e.g., by a graphics processing unit (GPU)) or another kind of specialized computing device.

In some implementations, portions of the fundus image diagnosis process can be implemented in both the client device 102 and the server system 108. For example, image preprocessing can be performed on the client device 102, such as anonymization (e.g., removing patient name, date of birth, or identification number, from a header of the medical image file), finding edge of the effective region of interest, or image normalization, and so on. The pre-processed fundus image can be received at the server system 108. The server system 108 can perform the DR prediction using a trained machine learning model.

In some implementations, after generating the prediction result, the server system 108 can send the prediction result to the client device 102 over the network 106. For example, the server system 108 can send a prediction score indicating whether or a likelihood that referable DR is represented in the fundus image to the client device 102 over the network 106. After receiving the prediction score, the client device 102 can store the prediction score on the client device 102. The client device 102 can display the prediction score and the fundus image to the doctor 112. The doctor 112 can perform diagnosis based on the fundus image and the prediction score generated by the computer aided diagnosis system.

In some implementations, for data security purposes, the server system 108, the client device 102 and the fundus camera 104 are located in the same medical facility (e.g., a hospital or a clinic). The network 106 includes a local area network (LAN) that connects one or more of the client device 102, the server system 108, and the fundus camera 104. The network 106 is disconnected from networks outside the medical facility. In some implementations, the server system 108 is located outside the medical facility (e.g., at a remote location outside an imaging center, a hospital or a clinic), while the client device 102 and the fundus camera 104 are located in the medical facility. The client device 102 or the fundus camera 104 can send the fundus image to the server system 108 over the network 106. After processing the fundus image using the computer aided diagnosis system, the server system 108 can send the prediction result back to the client device 102 over the network 106.

In some implementations, the example system 100 can include other types of medical devices 104 that generate medical data, such as an X-ray scanner, a Computed Tomography (CT) scanner, a Magnetic Resonance Imaging (MRI) scanner, a dental scanner, and so on. The medical device 104 can generate medical data (e.g., one or more medical images) that represents information of a patient's medical condition. Similar to the example of DR detection in a fundus image, the example system 100 can perform computer aided diagnosis from the medical data using machine learning and can generate diagnosis results. For example, the computer aided diagnosis system implemented in the server system 108 can detect one or more tumors in a set of CT images.

Figure 2:
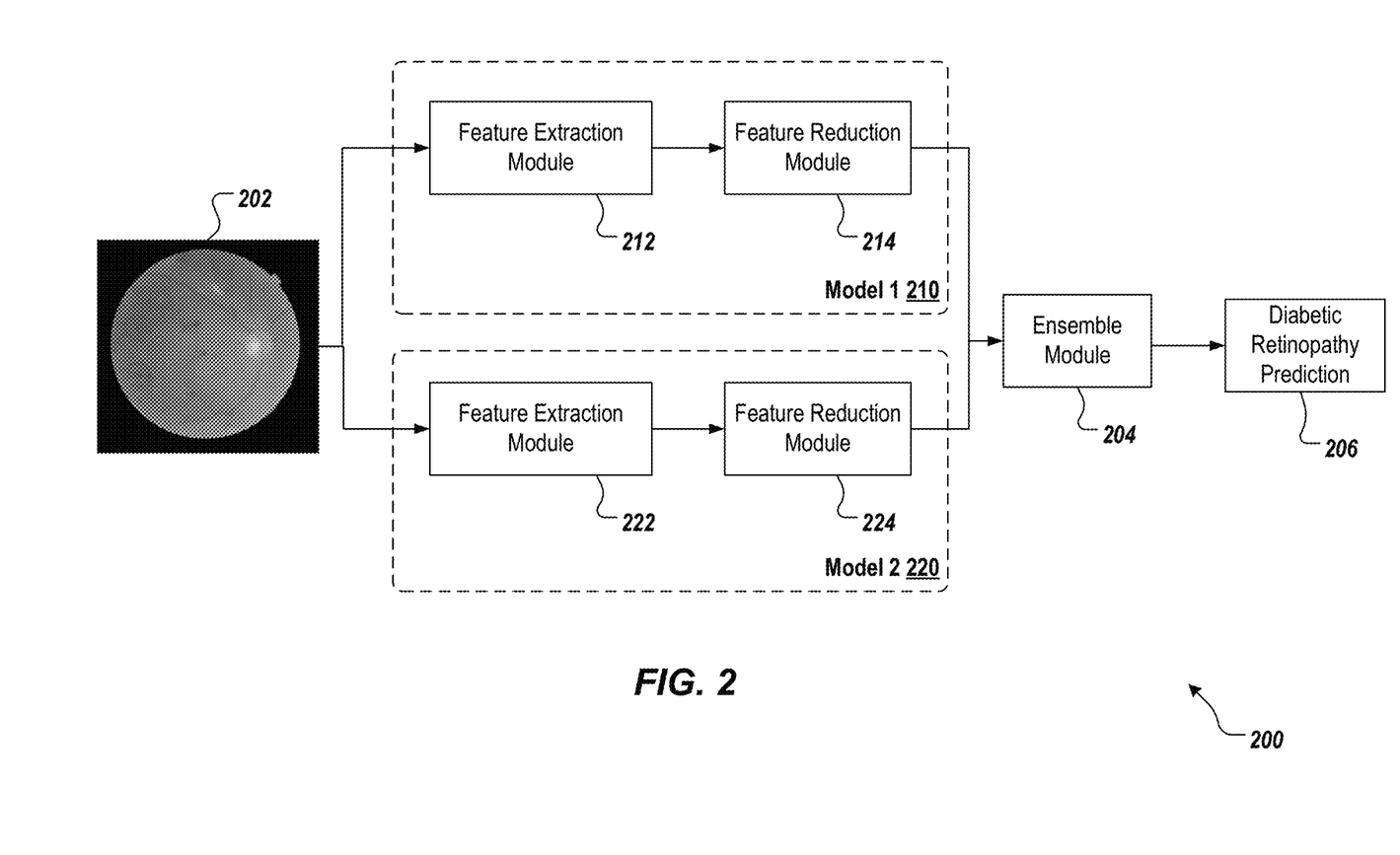
FIG. 2 depicts an example of a conceptual architecture of a machine learning model for diabetic retinopathy detection in a fundus image.

FIG. 2 depicts an example of a conceptual architecture 200 of a machine learning model for diabetic retinopathy detection in a fundus image. The conceptual architecture can be implemented in one or more computing devices, such as the example system 100 depicted in FIG. 1.

The example conceptual architecture 200 includes two or more machine learning models (e.g., model 1 (210) and model 2 (220)) and an ensemble module 204. Each machine learning model includes a feature extraction module and a feature reduction module. For example, the machine learning model 1 (210) includes a feature extraction module 212 and a feature reduction module 214, and the machine learning model 2 (220) includes a feature extraction module 222 and a feature reduction module 224. A fundus image 202 (also referred to as input image 202 herein) is provided as an input to the conceptual architecture 200, and a diabetic retinopathy (DR) prediction 206 is generated as an output.

The fundus image 202 is an input to the conceptual architecture 200 (i.e., the fundus image 202 is the input to the machine learning model 1 (210) and is the input to the machine learning model 2 (220)). The fundus image 202 is a digital photograph of the fundus and can be captured by the fundus camera 104. The fundus image 202 can be a color image with red and orange color indicating a region of interest (ROI) of the fundus over a black background. More particularly, the fundus image 202 is provided as a digital image represented as data, the data providing values for each of a plurality of pixels that the fundus image is composed of. In some examples, each pixel includes respective values for a blue channel, a green channel, a red channel, and an alpha channel, where alpha represents the opaqueness of the respective pixel (e.g., BGRa format). In some examples, the fundus image is processed to convert the pixel values to another color space. An example color space includes the hue, saturation, value (HSV) color space.

In some implementations, the fundus image 202 can be a pre-processed image generated from a raw fundus photography captured by the fundus scanner 104 through image pre-processing. The image pre-processing can include an eye tracking process that locates a region-of-interest (ROI) over the raw fundus image (i.e., the edge of the effective fundus photography). The raw fundus image can be cropped using the edge information such that the cropped fundus image can have a uniform size compared with other fundus images that are being processed by the machine learning model. The image pre-processing can include a Gaussian blur processing to normalize the color of the fundus image 202.

In some implementations, the input image 202 can include other types of medical images, such as one or more images or videos obtained from a medical imaging device. Examples of medical imaging devices include X-ray, CT, MRI, Ultrasound, PET, and so on. The input image 202 can capture one or more lesions or abnormalities in the body that was scanned. A system utilizing the conceptual architecture 200 of a machine learning model can perform computer aided diagnosis and can help doctors (e.g., radiologists) to make diagnostic decisions from the input image 202.

The feature extraction module 212 (or 222) can generate a feature representation of the input image 202. Generally, in machine learning and pattern recognition, feature extraction starts from an input data and builds derived values (i.e., a set of features or feature maps) intended to be informative about properties of the input data. For example, the feature extraction module 212 can generate feature representation of the features in the fundus image 202 (e.g., feature representations of the blood vessels, the dark spots, image intensities and their changes, small lesions, and so on). The feature representation can be a feature vector or a feature matrix. For example, the feature representation can be a feature vector that has length 2048. As another example, the feature representation can be a feature matrix with dimension 2048×2048×300.

The feature extraction module 212 (or 222) can include one or more layers of a convolutional neural network (CNN). The CNN includes a number of convolutional layers and each convolutional layer has parameters whose values define the convolutional filters for the layer. Each layer in CNN includes one or more neurons. A neuron in a neural network is a mathematical function that computes an output signal based on one or more input signals, and each neuron has learnable weights.

Example architectures of CNN include VGG network (Simonyan, Karen, and Andrew Zisserman. *"Very deep convolutional networks for large-scale image recognition."* arXiv preprint arXiv: 1409.1556 (2014)), Residual Neural Network (ResNet) (He, Kaiming, et al. *"Deep residual learning for image recognition."* Proceedings of the IEEE conference on computer vision and pattern recognition. 2016), Feature Pyramid Network (Lin, Tsung-Yi, et al. *"Feature pyramid networks for object detection."* Proceedings of the IEEE conference on computer vision and pattern recognition. 2017), any version of an Inception model, such as Inception-V4 (Szegedy, Christian, et al. *"Inception-v4, inception-resnet and the impact of residual connections on learning."* Proceedings of the AAAI Conference on Artificial Intelligence. Vol. 31. No. 1. 2017), and so on. For example, the feature extraction module 212 can include a modified Inception V4 model, which includes multiple layers of the Inception V4 model from the input layer to the last average pooling layer. More details of the feature extraction module 212 will be discussed in connection with FIG. 3.

The feature representation generated from the feature extraction module 212 can be a feature vector with a predetermined dimension that is determined by dimension of the input image 202 and the neural network architecture of the feature extraction module 212. In some implementations, the feature representation can be a feature vector and the dimension of the feature vector can be a large number (e.g., 2048, 4096, or 10000).

When the feature representation has too large of a dimension and captures random fluctuations and noise in the training data, the machine learning model can have overfitting and may not produce accurate predictions for unseen data. That is, overfitting happens when a machine learning model learns the details and noise in the training data to the extent that it negatively impacts the performance of the machine learning model on the new data.

Typically, a CNN model can include a dropout layer to overcome overfitting. Dropout is a technique where randomly selected neurons are ignored during training (i.e., they are "dropped-out" randomly). With a dropout layer, neurons cannot rely on other neurons to correct their mistakes, which reduces the number of co-adaptations that do not generalize well to unseen data, and reduces overfitting. However, dropout technique may significantly increase training time.

The feature reduction module 214 (or 224) in the example conceptual architecture 200 includes a sequence of feature reduction layers that replaces a dropout layer, and the last feature reduction layer generates a prediction result. For example, the machine learning model 1 (210) includes a feature reduction module 214 that replaces the dropout layer of an Inception V4 model.

The feature reduction module 214 (or 224) includes a sequence of feature reduction layers that combine the feature representation generated from the feature extraction module 212 and thus reduce the effect of unimportant features. The feature reduction module 214 can generate a sequence of feature representations with sequentially reducing sizes. For example, if the size of the feature vector generated from the feature extraction module 212 is 2048, the feature reduction module 214 can generate a sequence of feature representations with sequentially reducing sizes (e.g., 1024, 512, 256).

The last feature reduction layer of the feature reduction module 214 generates a prediction result. The last layer can be, for example, a classification layer or a regression layer. In some implementations, a classification layer can generate a likelihood score indicating the probability that the fundus image 202 has DR. For example, the feature reduction module can generate a score of 0.9 indicating a high likelihood that the fundus image 202 has referable DR. More details of the feature reduction module 214 (or 224) will be discussed in connection with FIG. 4.

The conceptual architecture 200 can include two or more machine learning models (e.g., model 1 and model 2 in FIG. 2) that are trained to detect DR from a fundus image. In some implementations, the two or more machine learning models can have the same CNN architecture. In some implementations, the two or more machine learning models can use different CNN architectures. In some implementations, the two or more machine learning models can be trained using the same training examples (training data). For example, model 1 and model 2 can use the same modified Inception V4 architecture and can be trained using the same training examples (training data). Note that even though model 1 and model 2 have the same architecture and are trained using the same training examples, the parameters of the two models are likely to be different.

The conceptual architecture 200 can include an ensemble module 204 that can calculate a final prediction result (e.g., DR prediction 206) based on the two prediction results generated by the two or more machine learning models (e.g., model 1 and model 2 in FIG. 2). The final prediction result can be an aggregated value based on the multiple prediction results from the multiple machine learning models. For example, the final prediction result can be the mean value, the maximum value, the medium value, the weighted average value, the root mean squared value of the multiple prediction results, or other representative value of the multiple prediction results. For example, when model 1 (210) generates a prediction score of 2.0 and model 2 (220) generates a prediction score of 3.0, the ensemble module 204 can generate a final DR prediction 206 with an average score of 2.5.

In some implementations, the conceptual architecture 200 of a machine learning model can include only one machine learning model, instead of two or more machine learning models. For example, the conceptual architecture 200 of a machine learning model can include machine learning model 1 (210), but may not include machine learning model 2 (220). When a single machine learning model can generate accurate predictions, the conceptual architecture 200 may not need to include an ensemble module 204 that ensembles prediction results from multiple machine learning models.

Figure 3:
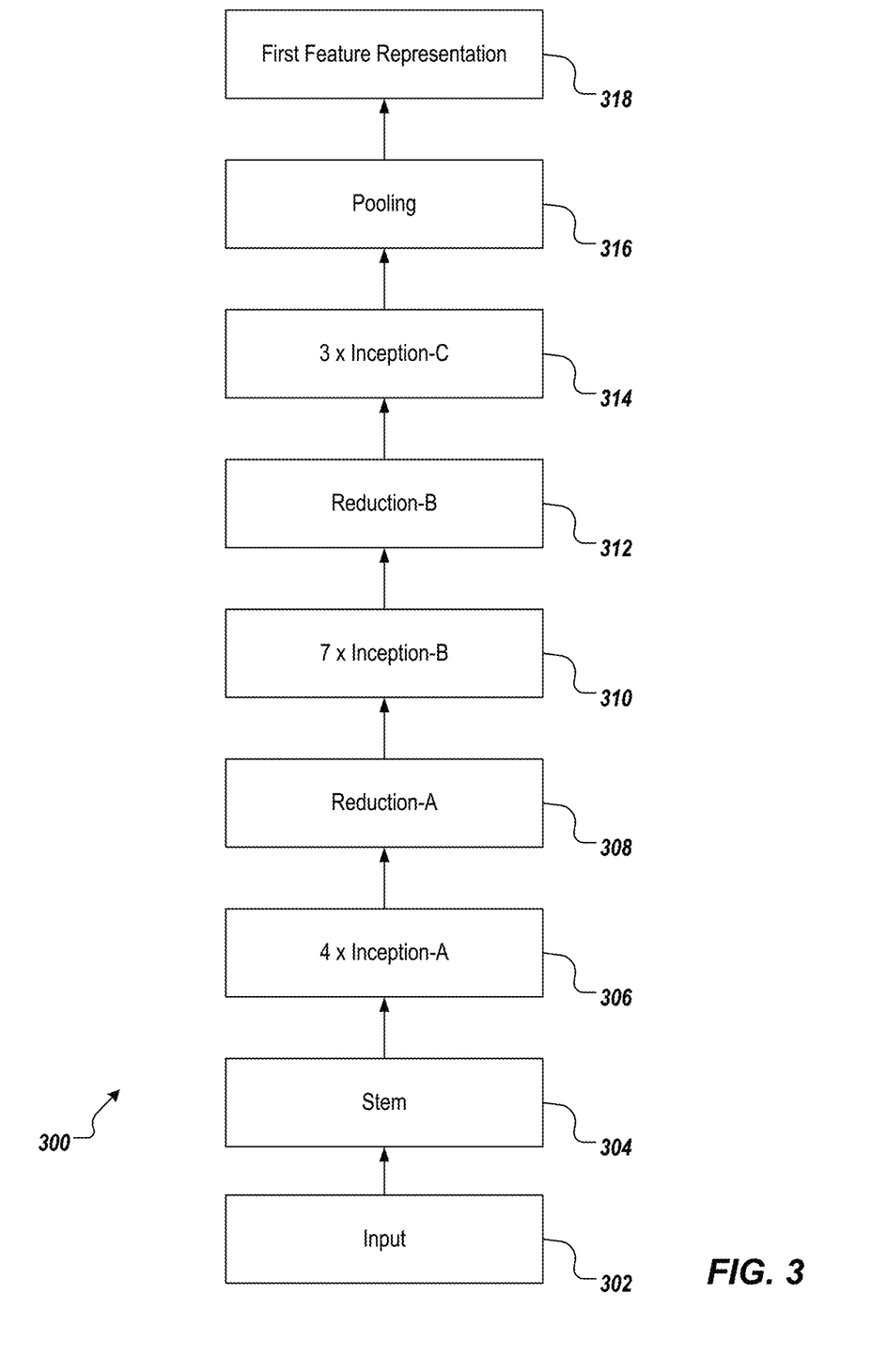
FIG. 3 depicts an example architecture of a feature extraction module.

FIG. 3 depicts an example architecture 300 of a feature extraction module. The example architecture 300 depicts a modified Inception-V4 model. The Inception-V4 model is a deep convolutional neural network model developed to solve image classification problems, which is described in detail in Szegedy, Christian, et al. "*Inception-v4, inception-resnet and the impact of residual connections on learning.*" *Proceedings of the AAAI Conference on Artificial Intelligence.* Vol. 31. No. 1. 2017, which is expressly incorporated herein by reference in the entirety.

The example architecture 300 takes an input image 302 as an input to the neural network model and generates a first feature representation 318 of the input image as an output. Unlike the Inception-V4 model, the example architecture 300 does not include the dropout layer and the softmax layer that would otherwise be configured after the pooling layer 316. Instead, the output from the example architecture 300 (i.e., the first feature representation 318) can be the output from the pooling layer 316. The first feature representation 318 can be provided as an input to the feature reduction module 214, which performs feature reduction and generates a prediction result.

The example architecture 300 includes a sequence of feature extraction layers including a Stem block 304, an Inception-A block 306, a Reduction-A block 308, an Inception-B block 310, a Reduction-B block 312, an Inception-C block 314, and a pooling layer 316.

Each block (e.g., the Stem block 304, the Inception-A block 306, the Reduction-A block 308, the Inception-B block 310, the Reduction-B block 312, and the Inception-C block 314) in the example architecture 300 can include a plurality of convolutional layers, pooling layers, concatenation layers, etc.

The Stem block 304 includes a set of preliminary convolutions performed before the Inception blocks. That is, the Stem block includes a sequence of convolution layers that perform initial feature extractions from an input image 302. The Stem block 304 includes multiple parallel and asymmetrical convolutional layers. The output feature representation from the Stem block has a reduced size in the width and height dimension, and has an increased size in the channel dimension. For example, the Stem block 304 can take an RGB color image with dimension 299×299×3 as input, and can generate a feature representation with dimension 35×35×384. Here, the width and height dimension is reduced from 299 to 35, and the channel dimension is increased from 3 to 384.

Each Inception block (e.g., Inception-A, Inception-B, and Inception-C) can include parallel convolutional layers with different sized convolutional filters (e.g., 1×1, 3×3, 5×5), and the results of the convolutional filters are concatenated.

Some convolutional filters can be asymmetrical. For example, the Inception-C block includes a 1×3 convolutional filter followed by a 3×1 convolutional filter. As another example, the Inception-C block includes a 1×3 convolutional filter that is parallel with a 3×1 convolutional filter.

Multiple Inception blocks can be grouped together to perform feature extraction. For example, 4× Inception-A 306 includes four identical Inception-A blocks that are sequentially connected with each other. Similarly, 7× Inception-B 310 includes seven identical Inception-B blocks and 3× Inception-C 314 includes three identical Inception-C blocks.

Each Reduction block (e.g., Reduction-A or Reduction-B) can reduce the size of the feature representation in the width and height dimension, and optionally, can increase the size in the channel dimension. The Reduction block can include one or more parallel convolutional layers and pooling layers that reduce the size of the feature representation in the width and height dimension. For example, the Reduction-A block can take a feature representation with a dimension of 35×35×384 as input and can generate an output feature representation with a dimension of 17×17×1024.

The pooling layer 316 can reduce the dimension of the output feature representation generated from the 3× Inception-C block 314 and can generate a first feature representation 318. The pooling layer 316 can be an average pooling layer or a max (or maximum) pooling layer. An average pooling layer can perform operations that calculate the average values for patches of a feature representation, and use these values to create a down-sampled (pooled) feature representation. A max pooling layer can perform operations that calculate the maximum, or the largest, values for the patches of the feature representation, and use these values to create a down-sampled (pooled) feature representation that highlights the most dominant features. In some implementations, the pooling layer 316 can generate a feature vector from a feature matrix (i.e., the width and height dimension of the feature representation is reduced to 1). For example, the pooling layer 316 can take a feature representation of a dimension 8×8×1536 as input and can generate a feature vector with length 1536.

In some implementations, the feature extraction module 214 can include other feature extraction algorithms, such as other deep convolutional neural networks, or other feature extractors. Examples of other deep convolutional neural networks include a modified ResNet and a modified Feature Pyramid Network. Examples of other feature extractors include Histogram of Oriented Gradient (HOG), Haar, Speeded Up Robust Features (SURF), and Scale-Invariant Feature Transform (SIFT) extractors.

Figure 4:
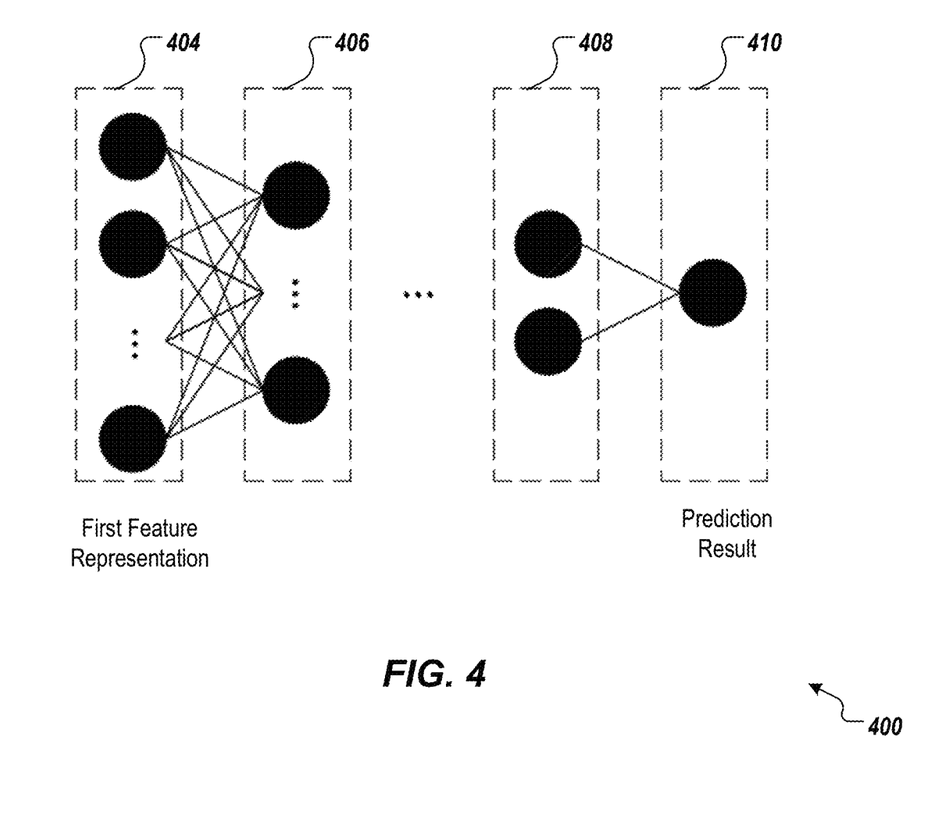
FIG. 4 depicts an example architecture of a feature reduction module.

FIG. 4 depicts an example architecture 400 of a feature reduction module. The feature reduction module includes a sequence of feature reduction layers (e.g., the feature reduction layers 406, 408, 410), and the last feature reduction layer (e.g., the feature reduction layer 410) generates a prediction result. The feature reduction module takes the first feature representation 404 generated from the feature extraction module 212 as input, and generates a prediction result 410 as an output.

Unlike a dropout layer in which randomly selected neurons are ignored during training, all of the neurons of the sequence of the feature reduction layers are activated and used during training of the model. All of the neurons of the sequence of the feature reduction layers are activated and are used during the inference of the model (i.e., during the generation of a prediction result for a new input image).

The sequence of feature reduction layers in the feature reduction module can include one or more convolutional layers or fully-connected layers, or a combination of both. The sequence of feature reduction layers can generate a sequence of second feature representations of the input image 202 (or 302) from the first feature representation 404 of the input image. The sequence of feature reduction layers can combine the values in the first feature representation generated from the feature extraction module 212 and thus reduce the effect of unimportant features (i.e., reduce overfitting).

Each second feature representation in the sequence of the second feature representations has a lower dimension than the first feature representation. An output dimension of the next layer in the sequence of layers is less than an output dimension of the current layer. Therefore, the unimportant features can be combined and the effect of the unimportant features can be reduced. The prediction result 410 generated from the last layer can be determined based on less features, instead of the relatively larger number of features in the first feature representation 404. Thus, the trained machine learning model has less overfitting problems and can generate more accurate prediction results.

For example, if the feature reduction module includes M layers (i.e., layers 1, 2, 3, . . . , j−1, j, j+1, . . . , M), and M is a positive integer larger than 1, the dimension of the output from the (j+1)-th layer is less than the dimension of the output from the j-th layer. That is, the number of neurons in the (j+1)-th layer is less than the number of the neurons in the j-th layer.

As depicted in FIG. 4, the example architecture 400 of the feature reduction module takes a first feature representation 404 as an input, and the first feature representation 404 can be a feature vector with a relatively large size (e.g., 2048). Each black circle in FIG. 4 represents a neuron in the feature vector. The feature reduction module can generate a sequence of second feature representations 406, 408, and 410, with sequentially reducing size, such as, 1024, 2, and 1.

Each second feature representation is generated from a preceding feature representation through an implementation of a fully-connected layer or a convolutional layer. For example, the second feature representation 406 is generated from the first feature representation 404 through a fully-connected layer. That is, each neuron in the second feature representation 406 is a combination of all of the neurons in the first feature representation 404. The fully-connected layer can define the number of neurons in the second feature representation 406. The number of neurons in the second feature representation 406 is defined to be less than the number of neurons in the previous feature representation 404. For example, the size of the second feature representation 406 can be 1024, which is half of the size of the first feature representation 404.

The dimension of the second feature representations can be an arithmetic sequence, a geometric sequence, and so on. In some implementations, the dimension of the second feature representations can be calculated as a result of a function, or can be descending numbers that are randomly determined. For example, if the dimension of the first feature representation is 2048, the dimensions of the second feature representations can be 1024, 512, 256, . . . , or 1648, 1248, 848, . . . , or 1200, 1000, 800, . . . , and so forth.

The last feature representation 410 is the output of the feature reduction module. The last feature representation 410 can be a prediction result. For example, the last feature representation 410 can be a prediction score that indicates a predicted likelihood that the fundus image 202 has referable DR.

In some implementations, the prediction result can be a classification result, and the output layer of the feature reduction module can include a classification layer. The number of output classes can include two or more classes. The classification result can include respective likelihood scores indicating a probability that the input image belongs to each of the two or more classes. For example, the prediction result 410 can include likelihood scores (e.g., 0.9 and 0.1) for two classes: DR class and NO DR class. As another example, the prediction result 410 can include five likelihood scores (e.g., 0.1, 0.2, 0.3, 0.3, and 0.1) for five classes: no DR, mild NPDR, moderate NPDR, severe NPDR, and PDR.

In some implementations, the prediction result can be a regression result, and the output layer of the feature reduction module can include a regression layer. For example, the prediction result can include a decimal score (e.g., 2.5) within a range from 0 to 4 that indicates the level of severity of the DR.

Figure 5:
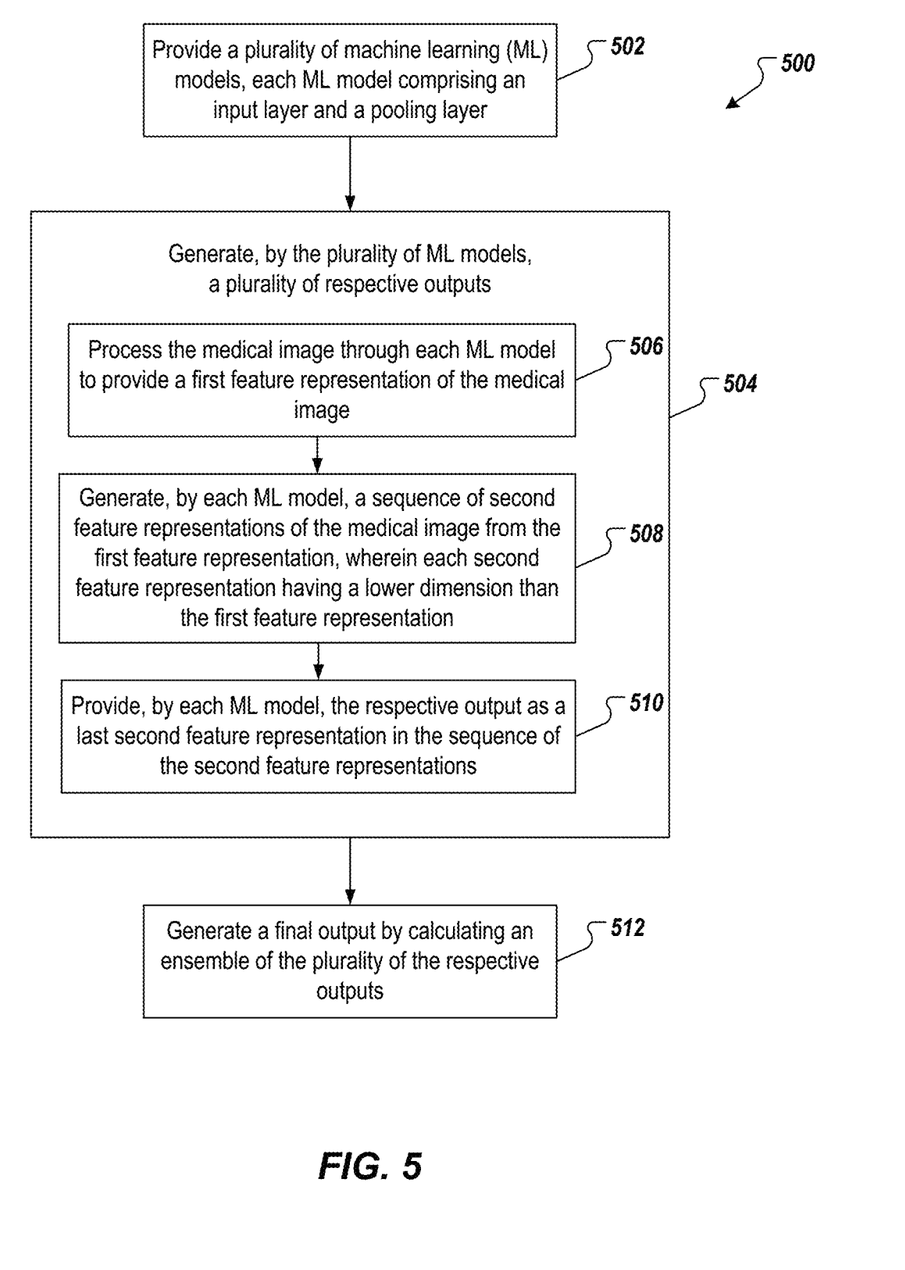
FIG. 5 depicts an example process for performing computer aided diagnosis using machine learning.

FIG. 5 is a flow chart of an example process 500 for performing computer aided diagnosis using machine learning. The example process 500 in FIG. 5 uses a forward inference pass through neural network models that have already been trained or are being trained to make computer aided diagnosis. The example process 500 can thus be used during training or to make predictions from unlabeled input (e.g., in a production system). The example process 500 will be described as being performed by an appropriately configured computer aided diagnosis system, such as the example system 100 in FIG. 1. In some implementations, the example process 500 may be performed using one or more computer-executable programs executed using one or more computing devices.

The system provides a plurality of machine learning (ML) models (502). Each ML model includes an input layer and a pooling layer. In some implementations, each ML model includes a feature extraction module and a feature reduction module. In some implementations, the feature extraction module can include a modified Inception-V4 model. In some implementations, the pooling layer can be an average pooling layer or a max pooling layer.

The system takes a medical image as input and generates, by the plurality of ML models, a plurality of respective outputs (504). For example, the medical image can be a fundus image, and the respective output can be a classification result indicating whether diabetic retinopathy (DR) is detected in the fundus image. The plurality of respective outputs can include a plurality of prediction scores. The system can generate a first prediction score using one machine learning model and the system can generate a second prediction score using another machine learning model.

For each ML model, the system performs the following steps, including step 506, step 508, and step 510, to generate the plurality of respective outputs.

The system processes the medical image through the ML model to provide a first feature representation of the medical image (506). In some implementations, the first feature representation is an output from the pooling layer. For example, the system can generate the first feature representation using a modified Inception-V4 model. The modified Inception-V4 model can generate the output from the last pooling layer, without using the dropout layer and the softmax layer in the original Inception-V4 model.

The system generates, by the ML model, a sequence of second feature representations of the medical image from the first feature representation of the medical image (508). Each second feature representation in the sequence of the second feature representations has a lower dimension than the first feature representation.

In some implementations, the system processes the first feature representation through a sequence of layers to generate the sequence of the second feature representations. In some implementations, the output dimension of the next layer in the sequence of layers can be less than the output dimension of the current layer. In some implementations, the output dimension of the sequence of layers can be an arithmetic sequence, or a geometric sequence. For example, the out dimension of the sequence of the layers can be 1024, 512, 256, and so on.

In some implementations, the sequence of layers includes one or more fully-connected layers or convolutional layers. For example, a layer in the sequence of layers can be a convolutional layer with filter size 1×1, and channel size N, where N is an integer that is larger than 1. As another example, a layer in the sequence of layers can be a fully-connected layer, where each output neuron is connected to all the input neurons. In some implementations, unlike a dropout layer, all neurons in the sequence of layers are used during training of and inference by the ML model. The system replaces the dropout layer with the sequence of feature reduction layers to improve training speed while reducing overfitting.

The system provides, by the ML model, the respective output as a last second feature representation in the sequence of the second feature representations (510). The last layer of the sequence of layers can be a classification layer or a regression layer. The respective output generated from the last layer can be a single number or can include multiple numbers. For example, the respective output can be a predicted likelihood that the fundus image has DR condition. As another example, the respective output can include predicted likelihood scores for multiple medical conditions in the fundus image (e.g., diabetic retinopathy, glaucoma, age-related macular degeneration, and so on).

The system generates a final output by calculating an ensemble of the plurality of the respective outputs (512). In some implementations, the final output can be a weighted average of the plurality of the respective outputs, or the final output can be a root mean-squared value of the plurality of the respective outputs. In some implementations, the final output can be a voting ensemble, such as one of the respective outputs selected by a majority voting method. By using the ensemble of the multiple ML models, the system can generate more accurate prediction results (e.g., higher sensitivity and/or higher specificity for detecting DR in fundus images).

The system can train each ML model using a plurality of training examples. The system can receive a plurality of training examples, each training example includes a medical image and a label indicating one or more medical conditions in the medical image. For example, each training example can include a fundus image, a label indicating whether the fundus image has a DR condition depicted therein.

The fundus images can be labeled by ophthalmologists. For example, two primary labelers can include board-certified ophthalmologists with at least one year of fellowship training in the field of retina. If the results are not consistent between the two primary labelers, a secondary labeler who is a board-certified ophthalmologist with at least 10 years of experience as a retina specialist would make the final diagnosis.

The system can use the training examples to train the ML model. The system can generate, for each medical image in the training example, a prediction result (e.g., a likelihood of DR being depicted in a fundus image). The system can compare the prediction results to the labels in the training examples. The system can calculate a loss which can measure the difference between the prediction results and the labels in the training examples. The loss can include one or more of: a classification loss, and a regression loss.

The classification loss can measure the difference between the predicted likelihood score of a condition and the label. The classification loss can include a cross-entropy loss, or a multi-class classification loss.

The regression loss can measure the distance between the predicted values to the labels, such as a root mean-squared distance, an absolute distance, and so on. For example, the predicted score can indicate the severity of DR (e.g., 2.5) while the label can include one of the following level scores: no DR=0, NPDR=1, moderate NPDR=2, severe NPDR=3, and PDR=4. The regression loss can include a root mean-squared distance loss that measures the distance between the predicted scores and the labels.

The system can then generate updated model parameter values based on the loss by using an appropriate updating technique (e.g., stochastic gradient descent with backpropagation). The system can then update the collection of model parameter values of the ML model using the updated model parameter values.

In some implementations, to speed up training, the training process can include two steps: (1) pre-training, and (2) fine-tune training. In the pre-training step, the system obtains a base model that had been trained on a large data set, such as the ImageNet dataset (Deng, Jia, et al. *"Imagenet: A large-scale hierarchical image database."* 2009 *IEEE conference on computer vision and pattern recognition. IEEE,* 2009). For example, the system can obtain an Inception-V4 model that has been trained on the ImageNet dataset (i.e., obtain a set of trained model parameter values for the model). The system can generate a pre-trained modified Inception-V4 model by removing the dropout layer and the softmax layer from the model. In the fine-tune training step, the system can take the set of trained model parameter values for the ML model and can use these as initialization to train the ML model using medical images. For example, instead of training from scratch, the system can train the modified Inception-V4 model initialized from the model parameter values obtained from pre-training.

In some implementations, the system can train multiple ML models using the same training examples. The system can further determine, using the training examples, an ensemble method to generate a final output from respective outputs generated from the multiple ML models. For example, the system can determine the weights of a weighted average ensemble using the training examples.

Implementations and all of the functional operations described in this specification may be realized in digital electronic circuitry, or in computer software, firmware, or hardware, including the structures disclosed in this specification and their structural equivalents, or in combinations of one or more of them. Implementations may be realized as one or more computer program products (i.e., one or more modules of computer program instructions encoded on a computer readable medium) for execution by, or to control the operation of, data processing apparatus. The computer readable medium may be a machine-readable storage device, a machine-readable storage substrate, a memory device, a composition of matter effecting a machine-readable propagated signal, or a combination of one or more of them. The term "computing system" encompasses all apparatus, devices, and machines for processing data, including by way of example a programmable processor, a computer, or multiple processors or computers. The apparatus may include, in addition to hardware, code that creates an execution environment for the computer program in question (e.g., code) that constitutes processor firmware, a protocol stack, a database management system, an operating system, or a combination of one or more of them. A propagated signal is an artificially generated signal (e.g., a machine-generated electrical, optical, or electromagnetic signal) that is generated to encode information for transmission to suitable receiver apparatus.

A computer program (also known as a program, software, software application, script, or code) may be written in any appropriate form of programming language, including compiled or interpreted languages, and it may be deployed in any appropriate form, including as a stand alone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry (e.g., an FPGA (field programmable gate array) or an ASIC (application specific integrated circuit)).

Processors suitable for the execution of a computer program include, by way of example, both general and special purpose microprocessors, and any one or more processors of any appropriate kind of digital computer. Generally, a processor will receive instructions and data from a read only memory or a random access memory or both. Elements of a computer can include a processor for performing instructions and one or more memory devices for storing instructions and data. Generally, a computer will also include, or be operatively coupled to receive data from or transfer data to, or both, one or more mass storage devices for storing data (e.g., magnetic, magneto optical disks, or optical disks). However, a computer need not have such devices. Moreover, a computer may be embedded in another device (e.g., a mobile telephone, a personal digital assistant (PDA), a mobile audio player, a Global Positioning System (GPS) receiver). Computer readable media suitable for storing computer program instructions and data include all forms of non-volatile memory, media and memory devices, including by way of example semiconductor memory devices (e.g., EPROM, EEPROM, and flash memory devices); magnetic disks (e.g., internal hard disks or removable disks); magneto optical disks; and CD ROM and DVD-ROM disks. The processor and the memory may be supplemented by, or incorporated in, special purpose logic circuitry.

To provide for interaction with a user, implementations may be realized on a computer having a display device (e.g., a CRT (cathode ray tube), LCD (liquid crystal display), LED (light-emitting diode) monitor, for displaying information to the user and a keyboard and a pointing device (e.g., a mouse or a trackball), by which the user may provide input to the computer. Other kinds of devices may be used to provide for interaction with a user as well; for example, feedback provided to the user may be any appropriate form of sensory feedback (e.g., visual feedback, auditory feedback, or tactile feedback); and input from the user may be received in any appropriate form, including acoustic, speech, or tactile input.

Implementations may be realized in a computing system that includes a back end component (e.g., as a data server), or that includes a middleware component (e.g., an application server), or that includes a front end component (e.g., a client computer having a graphical user interface or a Web browser through which a user may interact with an implementation), or any appropriate combination of one or more such back end, middleware, or front end components. The components of the system may be interconnected by any appropriate form or medium of digital data communication (e.g., a communication network). Examples of communication networks include a local area network ("LAN") and a wide area network ("WAN") (e.g., the Internet).

The computing system may include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the disclosure or of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products.

A number of implementations have been described. Nevertheless, it will be understood that various modifications may be made without departing from the spirit and scope of the disclosure. For example, various forms of the flows shown above may be used, with steps re-ordered, added, or removed. Accordingly, other implementations are within the scope of the to be filed claims.

What is claimed is:

1. A computer-implemented method for computer aided diagnosis of a medical image, the method comprising:

processing the medical image through a machine learning (ML) model to provide a first feature representation of the medical image, wherein the ML model comprises an input layer, a plurality of parallel convolution layers, and a pooling layer, wherein the first feature representation is an output from the pooling layer, the plurality of parallel convolution layers are configured with different sized convolution filters in which results processed by the different sized convolution filters are concatenated, and a concatenated output of the plurality of parallel convolution layers is inputted into the pooling layer;

generating, by the ML model, a sequence of second feature representations of the medical image, wherein a first second feature representation in the sequence of the second feature representations is generated from the first feature representation through a layer and has a smaller dimension than the first feature representation, each subsequent second feature representation in the sequence of the second feature representations is generated from a respective prior second feature representation through a layer and has a lower dimension than the first respective prior second feature representation; and generating, by the ML model, an output as a last second feature representation in the sequence of the second feature representations.

2. The method of claim 1, wherein each of the layers is a fully-connected layer or a convolutional layer.

3. The method of claim 2, wherein the output dimension of the sequence of layers is an arithmetic sequence, or a geometric sequence.

4. The method of claim 2, wherein all neurons in the sequence of layers are being used during training and inference of the ML model.

5. The method of claim 1, further comprising:

providing a plurality of ML models, each of the plurality of ML models comprising an input layer and a pooling layer;

generating, by the plurality of ML models, a plurality of respective outputs; and generating a final output by calculating an ensemble of the plurality of the respective outputs.

6. The method of claim 5, wherein the final output is one of a weighted average of the plurality of the respective outputs and a root mean-squared value of the plurality of the respective outputs.

7. The method of claim 5, wherein each of the plurality of ML models further comprises a modified Inception-V4 model, and wherein the pooling layer comprises an average pooling layer.

8. The method of claim 1, wherein the medical image is a fundus image, and wherein the output is a classification result indicating whether diabetic retinopathy is detected in the fundus image.

9. A system comprising one or more computers and one or more storage devices storing instructions that when executed by the one or more computers cause the one or more computers to perform operations comprising:

processing a medical image through a machine learning (ML) model to provide a first feature representation of the medical image, wherein the ML model comprises an input layer, a plurality of parallel convolution layers, and a pooling layer, wherein the first feature representation is an output from the pooling layer, the plurality of parallel convolution layers are configured with different sized convolution filters in which results processed by the different sized convolution filters are concatenated, and a concatenated output of the plurality of parallel convolution layers is inputted into the pooling layer;

generating, by the ML model, a sequence of second feature representations of the medical image, wherein a first second feature representation in the sequence of the second feature representations is generated from the first feature representation through a layer and has a smaller dimension than the first feature representation, each subsequent second feature representation in the sequence of the second feature representations is generated from a respective prior second feature representation through a layer and has a lower dimension than the respective prior second feature representation; and generating, by the ML model, an output as a last second feature representation in the sequence of the second feature representations.

10. The system of claim 9, wherein each of the layers is a fully-connected layer or a convolutional layer.

11. The system of claim 10, wherein the output dimension of the sequence of layers is an arithmetic sequence, or a geometric sequence.

12. The system of claim 10, wherein all neurons in the sequence of layers are being used during training and inference of the ML model.

13. The system of claim 9, the operations further comprise:

providing a plurality of ML models, each of the plurality of ML models comprising an input layer and a pooling layer;

generating, by the plurality of ML models, a plurality of respective outputs; and generating a final output by calculating an ensemble of the plurality of the respective outputs.

14. The system of claim 13, wherein the final output is one of a weighted average of the plurality of the respective outputs and a root mean-squared value of the plurality of the respective outputs.

15. The system of claim 13, wherein each of the plurality of ML models further comprises a modified Inception-V4 model, and wherein the pooling layer comprises an average pooling layer.

16. The system of claim 9, wherein the medical image is a fundus image, and wherein the output is a classification result indicating whether diabetic retinopathy is detected in the fundus image.

17. One or more non-transitory computer-readable storage media storing instructions that when executed by one or more computers cause the one or more computers to perform operations comprising:

processing a medical image through a machine learning (ML) model to provide a first feature representation of the medical image, wherein the ML model comprises an input layer, a plurality of parallel convolution layers, and a pooling layer, wherein the first feature representation is an output from the pooling layer, the plurality of parallel convolution layers are configured with different sized convolution filters in which results processed by the different sized convolution filters are concatenated, and a concatenated output of the plurality of parallel convolution layers is inputted into the pooling layer;

generating, by the ML model, a sequence of second feature representations of the medical image, wherein a first second feature representation in the sequence of the second feature representations is generated from the first feature representation through layer and has a smaller dimension than the first feature representation, each subsequent second feature representation in the sequence of the second feature representations is generated from a respective prior second feature representation through a layer and has a lower dimension than the respective prior second feature representation; and generating, by the ML model, an output as a last second feature representation in the sequence of the second feature representations.

18. The computer-readable storage media of claim 17, wherein each of the layers is a fully-connected layer or a convolutional layer.

* * * * *